United States Patent [19]

Thomas

[11] Patent Number: 5,330,755
[45] Date of Patent: Jul. 19, 1994

[54] PROCESS FOR THE PRODUCTION OF AN ANTI-DIARRHOEIC PRODUCT BASED ON CAROB

[75] Inventor: Remi Thomas, Berneuil en Bray, France

[73] Assignee: Nestec S.A., Vevey, Switzerland

[21] Appl. No.: 901,258

[22] Filed: Jun. 19, 1992

[30] Foreign Application Priority Data

Jul. 31, 1991 [EP] European Pat. Off. ........ 91112849.4

[51] Int. Cl.$^5$ ........................ A61K 35/78; A61L 2/08; C07C 69/88
[52] U.S. Cl. ................... 424/195.1; 422/26; 514/867; 560/68
[58] Field of Search ............. 424/195.1; 514/867; 422/26; 560/68

[56] References Cited

U.S. PATENT DOCUMENTS 4,999,197  3/1991  Würsch .................... 424/195.1
5,043,160  8/1991  Würsch .................... 424/195.1

FOREIGN PATENT DOCUMENTS 1191378  8/1985  Canada .
1020798  6/1950  France .

OTHER PUBLICATIONS

Loeb, H., Tannin-Rich Carob Pod for the Treatment of Acute-Onset Diarrhea, J of Pediatric Gastro & Nutrition 8: 480-485 1989.

Primary Examiner—Michael G. Wityshyn
Assistant Examiner—Ralph Gitomer
Attorney, Agent, or Firm—Vogt & O'Donnell

[57] ABSTRACT

Desugared carob pod is treated with superheated steam to pasteurize and dry the carob.

15 Claims, No Drawings

PROCESS FOR THE PRODUCTION OF AN ANTI-DIARRHOEIC PRODUCT BASED ON CAROB

BACKGROUND OF THE INVENTION

This invention relates to a process for the production of an anti-diarrhoeic product based on carob.

The anti-diarrhoeic properties of carob are well known. Thus, a composition containing 60 to 80% by weight roasted carob bean flour marketed under the name AROBON is known. However, this composition, which gives good results in the treatment of diarrhoea with no side effects, has the disadvantage of necessitating daily doses on the order of 20 g to 40 g which can give rise to problems of administration, particularly in young children.

Thus, European Patent Application Publication No. 214 317 describes an anti-diarrhoeic dietetic product containing a carob bean flour as active principle.

In this process, carob pods which have been shelled and crushed are ground in a mill and introduced into water. The sugars present in the carob and the tannins soluble in water at ambient temperatures are thus dissolved. After preparation of the liquid phase, a sugar-free product is collected.

To obtain a product freed from its microorganisms, the desugared carob is then introduced into a further quantity of water and pasteurized.

After pasteurization, the carob is reground so that it can be reduced to powder and spray-dried before being finally ground to a particle size enabling it to be suspended in a liquid.

Although the product obtained has all the characteristics of an effective anti-diarrhoeic agent coupled with considerable ease of administration by comparison with the prior art, it has several disadvantages in regard to the process used for its production.

In the first place and as explained in European Patent Application Publication No. 214 317, the anti-diarrhoeic effect is obtained through the presence of tannins in condensed forms which are insoluble in cold or tepid water and, more particularly, are insoluble at body temperature. Thus, these tannins enter the intestine without being degraded by gastric acid or inactivated by proteins. Accordingly, they perform a depurative and antiseptic function without intervening in the physiological processes.

Accordingly, in order to obtain an effective anti-diarrhoeic product, it is crucial to avoid solubilization of the tannins present in the desugared carob. Now, this solubilization process begins at temperatures of the order of 90° C. and is considered to be complete at temperatures of the order of 120° C.

Accordingly, this limits the pasteurizing treatment which is carried out at around 95° C.

Accordingly, the end product obtained contains at least 20% by weight native tannins (expressed as total polyphenols) with a ratio by weight of soluble tannins to insoluble tannins of less than 0.37 for solubility measurement at 37° C.

In the second place, the drying process is uneconomical because it follows a considerable addition of water required for pasteurization, the product having a dry matter content before drying of 20% to 25% by weight.

Accordingly, the problem addressed by the present invention was to provide a process for the production of an anti-diarrhoeic product of the type described in European Patent Application Publication No. 214 317 in which the pasteurization step could be carried out at much higher temperatures without solubilization of the tannins and which, in addition, would enable the pasteurization and drying steps to be carried out in a single stage.

The use of superheated steam for pasteurizing food products has been known for some time, cf. for example French Patent No. 1 020 798.

In addition, European Patent No. 58 651 describes a process and an apparatus for treating animal foods with superheated steam.

By means of this process and apparatus for treatment with superheated steam, it is possible to dry the product to be treated in proportions dependent on the treatment parameters of pressure and temperature of the superheated steam and treatment time.

SUMMARY OF THE INVENTION

Now, it has been found that it is possible to apply treatment with superheated steam to desugared carob at temperatures distinctly higher than 120° C. without any sign of solubilization of the tannins. It is thus possible in a single step to pasteurize and dry the desugared carob.

Accordingly, the present invention relates to a process for the production of an anti-diarrhoeic product based on carob in which carob pods which have been shelled and ground are desugared in aqueous medium, the aqueous phase obtained is subsequently separated from the solid phase and the solid residue obtained is then simultaneously dried and pasteurized by treatment with superheated steam.

DETAILED DESCRIPTION OF THE INVENTION

The first step of the process according to the invention comprises preparing the carob for pasteurization and preliminary drying. This may be done by the method described in European Patent Application Publication No. 214 317.

Carob pods which have been shelled and crushed into pieces 1 to 2 cm in size are subjected to grinding in a mill and to extraction of the sugars. These two steps may be carried out separately, grinding being carried out first, and extraction of the sugars then being carried out by suspending the carob in a certain quantity of water. Extraction of the sugars is preferably carried out by immersion of 1 part by weight carob in 11 parts by weight water for 30 minutes. Grinding may also be carried out in a colloid mill which enables the carob to be simultaneously desugared.

The water is then partly extracted from the desugared carob, for example by centrifugation or pressing.

After the water extraction step, the product is present in the form of aggregates. To facilitate the operations of dosing and drying, it can be useful to break up these aggregates, for example in a hammer mill. The product obtained in this way flows freely without solidifying and then has to be dried and pasteurized to obtain the end product.

The pasteurizing and drying steps are carried out simultaneously by treatment with superheated steam.

The treatment with superheated steam may be carried out using an apparatus of the type described in European Patent No. 58 651 cited above.

The superheated steam is obtained by heating steam to a temperature above its saturation temperature.

The treatment may be carried out at atmospheric pressure or at a pressure above atmospheric pressure. In this case, the steam is obtained by superheating saturated steam kept under pressure.

Superheated steam always tends to return to the state of saturated steam without losing its sensible heat. This sensible heat may thus be used to evaporate water and hence to dehydrate a product.

In European Patent No. 58 651, vertical tubes are interconnected by U tubes. These vertical tubes comprise a double jacket fed with steam for superheating the steam circulating inside the tubes.

Upstream of the first tube, a feed system comprising a hopper, a first lock and a steam injection unit, for example in the form of a fan, enables the product to be introduced into and dispersed in the superheated steam.

Downstream of the last tube, a cyclone separates the treated product from the steam. The steam is recycled and superheated in a heat exchanger before being reintroduced by a fan into the tube circuit. The treated product is removed from the cyclone through a second lock. The locks also ensure the maintenance of pressure in the tube circuit used for the treatment. A system of valves enables the pressure in the treatment circuit to be regulated by injection or extraction of steam.

In this type of arrangement, the product to be treated is introduced under pressure through the first lock. The product is dispersed in the flow of superheated steam which then transports the product into the tube circuit.

During its treatment with superheated steam, the product passes from ambient temperature to the saturation temperature and is then dried in a first step. The saturation temperature depends on the pressure of the saturated steam.

EXAMPLE I

It was essential at the outset to prove that the treatment with superheated steam did not result in solubilization of the tannins present in the desugared carob. To this end, the desugared carob was treated with superheated steam at three different pressures and hence, at three different saturation temperatures.

The level of solubilization of the tannins is measured as follows: 5 g of the end product obtained after the treatment with superheated steam are suspended in 100 cc water. The suspension is stirred and its coloration is compared with the coloration of an aqueous suspension obtained from desugared carob which has not been treated with superheated steam (control).

The results are set out in the following Table where the treatment time is shown in the form of an upper limit, not all the particles moving at the same speed in the installation.

| Treatment conditions | Test A | Test B | Test C |
|---|---|---|---|
| Steam temperature (°C.) | 153 | 180 | 198 |
| Saturation temperature (°C.) | 102 | 111 | 134 |
| Relative steam pressure (bar) | 0.1 | 0.5 | 2 |
| Treatment time | 18–20 s | 19–50 s | 19–50 s |
| Coloration | None | None | None |

It can thus be seen that, during the treatment with superheated steam, there is no solubilization of the tannins in spite of temperatures distinctly higher than 120°

C. Measurements carried out by spectrometry confirmed the absence of solubilization of the tannins.

EXAMPLE II

Various tests were carried out in which
the input of product into the installation,
the initial dry matter content of the product,
the pressure (and hence the saturation temperature) and
the dry temperature of the steam introduced, as measured at the input fan
were all varied.

During these tests, the treatment time of the product was between 15 and 60 seconds and the steam injection rate was between 26 and 28 m/s.

In addition, the dry temperature of the steam was measured in the first tube and in the last tube of the installation. This is because the temperature in question develops during the treatment. More particularly, because the steam gives off a large part of its sensible heat in the first tube, its temperature can fall to the level of the saturation temperature. This should be avoided because it can result in a reduction in the rate of flow of the steam and can block the installation by accumulation of non-transported product. The temperature of the steam then rises in the installation by virtue of the double jackets surrounding the tubes.

EXAMPLE III

Finally, the dry matter content of the end product and the quantity of water evaporated per hour (in kg/h) were measured.

The results of the tests are set out in the following Table, the steam pressure being shown as a relative value in relation to atmospheric pressure.

| Test | 1 | 2 | 3 | 4 | 5 | 6 | 7 | 8 |
|---|---|---|---|---|---|---|---|---|
| Input of product (kg/h) | 10 | 10 | 10 | 15 | 20 | 30 | 40 | 60 |
| Dry matter content of product (%) | 30.6 | 30.6 | 31.6 | 31.6 | 31.2 | 31.2 | 31.2 | 35.7 |
| Steam pressure (bar) | 0.5 | 2.0 | 0.5 | 0.5 | 0.5 | 0.5 | 0.5 | 0.5 |
| Steam saturation temperature (°C.) | 111 | 134 | 111 | 111 | 111 | 111 | 111 | 111 |
| Steam temperature at fan (°C.) | 180 | 198 | 195 | 192 | 198 | 198 | 197 | 200 |
| Final dry matter content (%) | 96.8 | 89.8 | 97.3 | 97.1 | 96.1 | 94.6 | 91.7 | 87.6 |
| Water evaporated (kg/h) | 6.84 | 6.50 | 6.75 | 10.12 | 13.51 | 20.11 | 26.39 | 35.56 |

It can be seen that, as mentioned above, the temperature of the steam does not cause solubilization of the tannins, nor is there any sign of burning on the product.

The key criterion to be taken into account for the choice of the steam temperature so far as the effectiveness of drying is concerned is the difference between the temperature of the steam injected into the installation, as measured at the input fan, and the saturation temperature which is itself determined by the steam pressure. For a constant steam temperature, an increase in pressure reduces the efficiency of evaporation.

This is clearly illustrated by the following Table 5 which shows the influence of the difference between these two temperatures on the final dry matter content of the product.

| | Influence of the difference between the temperature of the steam introduced and its saturation temperature | | | | | | | |
|---|---|---|---|---|---|---|---|---|
| Test | 1 | 2 | 3 | 4 | 5 | 6 | 7 | 8 |
| Input of product (kg/h) | 10 | 10 | 10 | 15 | 20 | 30 | 40 | 60 |
| Dry matter content of product (%) | 30.6 | 30.6 | 31.6 | 31.6 | 31.2 | 31.2 | 31.2 | 35.7 |
| Steam pressure (bar) | 0.5 | 2.0 | 0.5 | 0.5 | 0.5 | 0.5 | 0.5 | 0.5 |
| Steam saturation temperature (°C.) | 111 | 134 | 111 | 111 | 111 | 111 | 111 | 111 |
| Steam temperature at fan (°C.) | 180 | 198 | 195 | 192 | 198 | 198 | 197 | 200 |
| Temperature difference (°C.) | 69 | 64 | 84 | 81 | 87 | 87 | 86 | 89 |
| Final dry matter content (%) | 96.8 | 89.8 | 97.3 | 97.1 | 96.1 | 94.6 | 91.7 | 87.6 |
| Water evaporated (kg/h) | 6.84 | 6.50 | 6.75 | 10.12 | 13.51 | 20.11 | 26.39 | 35.56 |

It can thus be seen, more particularly from Tests 1, 2 and 3 that, for very similar quantities of water evaporated per hour and for the same rate of introduction of desugared carob, the final dry matter content is directly related to the temperature diference in question.

In addition, the following Table illustrates the influence of the quantity of water to be evaporated on the reduction in temperature of the steam in the first tube and on the final dry matter content, all the tests having been carried out at a relative steam pressure of 0.5 bar.

The quantity of water to be evaporated, i.e., the quantity of water introduced into the installation, is proportional to the input and inversely proportional to the initial dry matter content.

| | Influence of the quantity of water to be evaporated on the reduction in temperature in the first tube and on the final dry matter content | | | | | | |
|---|---|---|---|---|---|---|---|
| Test | 1 | 3 | 4 | 5 | 6 | 7 | 8 |
| Input of product (kg/h) | 10 | 10 | 15 | 20 | 30 | 40 | 60 |
| Dry matter content of product (%) | 30.6 | 31.6 | 31.6 | 31.2 | 31.2 | 31.2 | 35.7 |
| Steam pressure (bar) | 0.5 | 0.5 | 0.5 | 0.5 | 0.5 | 0.5 | 0.5 |
| Steam temperature at fan (°C.) | 180 | 195 | 192 | 198 | 198 | 197 | 200 |
| Steam temperature in tube 1 (°C.) | 149 | 157 | 145 | 148 | 136 | 126 | 121 |
| Temperature difference (°C.) | 31 | 38 | 47 | 50 | 62 | 71 | 79 |
| Final dry matter content (%) | 96.8 | 97.3 | 97.1 | 96.1 | 94.6 | 91.7 | 87.6 |
| Water evaporated (kg/h) | 6.84 | 6.75 | 10.12 | 13.51 | 20.11 | 26.39 | 35.56 |

It can clearly be seen that, the larger the quantity of water to be evaporated, the greater the temperature reduction in the first tube and the greater the reduction in the dry matter content of the end product even though the quantity of water evaporated per hour increases.

In order, therefore, to obtain an end product having a dry matter content of at least 90% by weight, the steam has to be injected at a temperature at least 60° C. and preferably at least 70° C. above its saturation temperature.

The final preferred conditions selected for the treatment with superheated steam were as follows:

| | |
|---|---|
| superheated steam temperature | 200° C. |
| steam pressure (relative) | 0.5 bar |
| steam injection rate | 27 m/s |
| residence time of product | 20 to 60 s |
| input rate of product | 30 kg/h |

By treating the desugared carob with these parameters, the end product obtained had a dry matter content of 25% by weight and a content of 23.2% by weight, based on dry matter, of tannins expressed as total polyphenols made up of 0.8% soluble tannins and 22.4% insoluble tannins, i.e. a ratio of soluble tannins to insoluble tannins of less than 0.04.

Finally, the pasteurization obtained is very effective as shown in the following Table, pasteurization being more effective, the higher the steam pressure.

| Germs | Product after treatment | Product after treatment |
|---|---|---|
| Revivifiable mesophilic germs/g | 150,000 | <3,000* |
| Coliforms/g | >3,000 | <10 |
| Faecal coliforms/g | >10 | None |
| Staphyloccocus aureus | None | None |
| Clostridium sulfito reducers | None | None |
| Yeasts/g | 4,300 | None |
| Moulds/g | 160 | None |

*Detection limit of analysis

Accordingly, the treatment according to the invention enables the product to be very efectively decontaminated, the germs being reduced by a factor of more than 1,000.

I claim:

1. A process for producing a carob product comprising treating ground, desugared carob pod with superheated steam to pasteurize and dry the carob.

2. A process according to claim 1 wherein the superheated steam has a temperature which exceeds its saturation temperature by at least 60° C.

3. A process according to claim 1 wherein the superheated steam has a temperature which exceeds its saturation temperature by at least 70° C.

4. A process according to claim 1 wherein the carob is treated with superheated steam at atmospheric pressure.

5. A process according to claim 1 wherein the carob is treated with superheated steam at a pressure above atmospheric pressure.

6. A process for producing a carob product comprising immersing carob pod in water to obtain an extract containing desugared carob, separating the desugared carob from the extract, and treating the separated desugared carob with superheated steam to pasteurize and dry the carob.

7. A process according to claim 6 wherein the desugared carob is separated from the extract by pressing the desugared carob.

8. A process according to claim 6 wherein the desugared carob is separated from the extract by centrifuging the desugared carob.

9. A process according to claim 6 wherein the superheated steam has a temperature which exceeds its saturation temperature by at least 60° C.

10. A process according to claim 6 wherein the superheated steam has a temperature which exceeds its saturation temperature by at least 70° C.

11. In a process for producing a carob product wherein carob pod is shelled, ground, desugared and dried, the improvement comprising treating the desugared carob with superheated steam to pasteurize and dry the carob.

12. A process according to claim 11 wherein the superheated steam has a temperature which exceeds its saturation temperature by at least 60° C.

13. A process according to claim 11 wherein the superheated steam has a temperature which exceeds its saturation temperature by at least 70° C.

14. A process according to claim 11 wherein the carob is treated with superheated steam at atmospheric pressure.

15. A process according to claim 11 wherein the carob is treated with superheated steam at a pressure above atmospheric pressure.

* * * * *